(12) United States Patent
Graber et al.

(10) Patent No.: US 6,255,254 B1
(45) Date of Patent: *Jul. 3, 2001

(54) CONCENTRATED COMPOSITIONS CONTAINING AGRICULTURALLY-ACTIVE MATERIAL

(75) Inventors: Gérard Graber; Alain Bossy, both of Lyons (FR)

(73) Assignee: Aventis CropScience SA, Lyons Cedex (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/288,997
(22) PCT Filed: Apr. 22, 1994
(86) PCT No.: PCT/FR94/00458
§ 371 Date: Oct. 25, 1995
§ 102(e) Date: Oct. 25, 1995
(87) PCT Pub. No.: WO94/24861
PCT Pub. Date: Nov. 10, 1994

Related U.S. Application Data

(63) Continuation of application No. 08/532,824, filed on Oct. 25, 1995, now abandoned.

(30) Foreign Application Priority Data

Apr. 28, 1993 (FR) .................................................. 93 05263

(51) Int. Cl.$^7$ .................................................. A01N 25/14
(52) U.S. Cl. .......................... 504/367; 424/409; 424/489; 514/952
(58) Field of Search ................................... 504/116, 367; 424/409, 489; 514/952

(56) References Cited

U.S. PATENT DOCUMENTS

| 3,877,928 | * | 4/1975 | Houston et al. | 504/116 |
| 5,222,595 | * | 6/1993 | Gouge et al. | 206/205 |
| 5,266,553 | * | 11/1993 | Champion et al. | 504/206 |

FOREIGN PATENT DOCUMENTS

| 48333/90 | 8/1990 | (AU) . |
| 10764/92 | 8/1992 | (AU) . |
| 34437/93 | 9/1993 | (AU) . |
| 37048/93 | 11/1993 | (AU) . |
| 44324/93 | 2/1994 | (AU) . |
| 60708/94 | 11/1994 | (AU) . |
| 0 544 602 A1 | 11/1992 | (EP) . |
| WO 90/02486 | 3/1990 | (WO) . |
| WO 92/12637 | 8/1992 | (WO) . |
| WO 92/15197 | 9/1992 | (WO) . |
| WO 93/05652 | 4/1993 | (WO) . |
| WO 93/25074 | 12/1993 | (WO) . |

OTHER PUBLICATIONS

Dobrat et l., CIPAC Handbook, "*Physico–chemical Methods for Technical and Formulated Pesticides,*" vol. F (1995) pp. 424–429.

* cited by examiner

Primary Examiner—S. Mark Clardy
(74) Attorney, Agent, or Firm—Morgan & Finnegan, LLP

(57) ABSTRACT

Solid concentrated compositions comprising at least two active substances used in agriculture. The compositions are characterized by being a mixture of concentrated compositions in the form of granules capable of being diluted in water, and in that their content of inhalable particles is less than 0.1%, and preferably less than 0,01%, and in that each granule capable of being diluted in water includes a maximum of one active substance. The invention also concerns a container system comprising such a solid concentrated agrochemical composition in a bag, the wall of which is a water soluble or dispersable material.

32 Claims, 1 Drawing Sheet

CONCENTRATED COMPOSITIONS CONTAINING AGRICULTURALLY-ACTIVE MATERIAL

This is a continuation of application Ser. No. 08/532,824, filed on Oct. 25, 1995 now abandoned.

The present invention relates to new concentrated compositions comprising at least 2 agriculturally-active materials, to the use of these concentrated compositions in the treatment of plants and to a containerization system comprising such a composition.

Many agriculturally-active materials are used with the aim of obtaining better results and better yields of crops.

In the present invention, the term agriculturally-active materials is understood to mean any kind of active material used in agriculture (including cultivation of gardens and green spaces) such as plant protection agents, agrochemical products, pesticides, growth regulators or plant nutrition agents. The pesticides are more particularly herbicides, insecticides, fungicides, nematocides and acaricides.

The majority of these active materials are manufactured and marketed in the form of concentrated compositions which are then applied by the farmer in the form of compositions which have been diluted with water, after having mixed the said concentrated compositions with water in the tank of a spray device for pesticidal treatment.

Concentrated compositions for dilution with water are provided in various forms well known to those skilled in the art. A particularly advantageous form for the user, that is to say the farmer, is presentation as dispersible granules.

The term dispersible granule is understood to mean a solid and cohesive agglomerate of constituent particles, the said particles having a size between 1 and 20 $\mu$m, which, after mixing with water, disintegrates or disperses to give a homogeneous and stable suspension. Within the meaning of the present invention, a dispersible granule does not denote a granule which, applied as such, while dry, to the soil, can however disintegrate at the end of a certain time spent in the environment. Presentation as a dispersible granule offers to the user a great convenience of use which makes it very desirable. The preparation of these dispersible granules is generally carried out from wettable powders which have the same chemical composition as the granules and whose particle size characteristics are those defined above for the constituent particles of the granules. These wettable powders are moistened, shaped and finally dried. This operation leads directly to the formation of moist granules, which it is then advisable to dry in order to obtain marketable granules.

Moreover, many agriculturally-active materials only destroy a portion of the harmful species against which the farmer wishes to protect his crop. For example, in the case of a herbicidal treatment, a given active material can only provide for the destruction of weeds of graminaceous type, or else only provide for the destruction of weeds of dicotyledonous type, or alternatively provide for the destruction of an adventitious plant against which the other active materials are without effect.

The farmer must therefore frequently resort to the simultaneous application of a number of active materials in order to solve his specific plant protection treatment problem.

Now, the relative importance of the harmful species present in the same population is capable of varying widely according to the geographic location of the cultivated area to be treated, so that it is necessary for the farmer to adapt the relative amounts of the active materials which he applies and to spray a diluted composition comprising the active materials according to a well-determined ratio.

The farmer can, with this aim, resort to the practice described as "at the time of use" or "tank-mix", that is to say to mixing a number of concentrated compositions, each containing a single active material, with the water contained in the tank of a sprayer. Such a practice is not, however, without danger. In effect, due to problems of compatibility between the concentrated compositions in the tank of the spraying device, application on the cultivated area of the active materials may not be homogeneous, which leads to the presence, on certain parts of the field, of an excessive amount of active materials and, in contrast, the presence on other parts of the field of an insufficient amount of active materials. This can be reflected now by phytotoxicity, now by absence of effectiveness.

The farmer can also, with the same aim of making his plant protection treatment better suited to the relative importance of the harmful species present on the cultivated area, use marketed ready-to-use concentrated compositions known under the name "ready mix". In this case, the availability of a product which leads to a homogeneous application of the active materials is provided for. However, the relative importance of the active materials in this product is set by the manufacturer and can be very far from that which the relative importance of the harmful species present in the population of harmful species in the area of the farmer would make necessary. In order to overcome this disadvantage, the manufacturer may make available to farmers a number of concentrated compositions combining the same active materials in different ratios.

The manufacture of a large number of such concentrated compositions, which makes it more convenient for the farmer to employ dispersible granules, leads, however, to a certain number of disadvantages and difficulties for the manufacturer.

In fact, the manufacture of dispersible granules requires particularly fine and sensitive controlling, for lack of which powder agglomerates or granules are obtained whose size lies outside the specification which the manufacturer wishes to observe. The granulation of a number of wettable powders comprising the same active materials at different contents, necessary for obtaining the corresponding dispersible granules, thus multiplies these difficult process controls for the manufacturer.

The granulation stage of a wettable powder must then be followed, on completion and before any new use of the apparatus, in other words at each change in manufacturing class, by a complete cleaning of the apparatus, made necessary by the presence of residual agglomerates of moist powder which adhere to the walls. When it is necessary to produce many dispersible granules comprising the same active materials at different contents, the category changes and the number of cleanings which result therefrom are accordingly necessarily multiplied.

Finally, the existence of a large number of products comprising the same active materials at different contents requires particularly significant corresponding stock control and monitoring work on the part of the manufacturer.

An aim of the present invention is to overcome the disadvantages of the known concentrated compositions.

Another aim of the present invention is to provide a concentrated composition suited to the specific plant protection problem of the farmer.

Another aim of the present invention is to provide a solid concentrated composition in which the air-borne particles content is reduced.

Another aim of the present invention is to make possible improved stock control by the manufacturer.

Another aim of the present invention is to provide concentrated pesticidal compositions which are easier to manufacture.

Another aim of the present invention is to provide concentrated pesticidal compositions whose manufacture is easier to control.

Another aim of the present invention is to provide concentrated pesticidal compositions whose manufacture is faster, due to the reduction in the number of changes in classes.

Another aim of the present invention is to provide a new containerization system comprising plant protection agents having one or a number of the following advantages:

contact of the agrochemical product with the user or the manufacturer or the handler of the product is avoided.

the agrochemical product is left in contact with the water where it must be dispersed and/or dissolved, avoiding accidental contact of concentrated product either with the environment or with human beings or animals.

the agrochemical product can be provided in units having a predetermined amount of active material, avoiding the necessity of measuring active materials and toxic or potentially toxic product.

Another aim of the present invention is to provide a new system for presenting agriculturally-active materials simultaneously having the following qualities:

it is self-dispersible, that is to say that it requires a minimum of energy and of time in order to be dispersed and diluted in the spray tank (containing water).

there is no contact of active materials with the user (farmer, haulier, handler).

the container remaining after use of the product no longer contains any trace of residue.

no cleaning of the containers which have contained agrochemical products need take place after use.

It has now been found that these aims could be achieved, entirely or partially, by virtue of the compositions and containerization systems according to the invention.

In the disclosure of the present invention, all the percentagaes shown are, except when otherwise specified, percentages by weight.

Moreover, the following definitions are used hereinbelow for the expressions "air-borne particles content" and "degree of friability".

The term air-borne particles is understood to mean particles with a size of less than 10 μm, preferably less than 5 μm, which are capable of appearing during any handling of the granules, especially during the pouring thereof, and which, due to their size, can, when carried by air, enter into the respiratory tracts of farmers or process workers.

The air-borne particles content is measured according to the method explained below.

The principle of the method consists in dropping a known amount of granules into a closed measuring chamber, so as to produce air-borne particles, and in then collecting them on a filter by means of a suction device and thus determining the corresponding mass. A microporous filter placed on the filter cartridge of a filtration device is weighed. The filtration device is connected to a flow meter and to a vacuum pump which is regulated so that the air flow rate is adjusted to 15 liters per minute. 30 g of granules to be analyzed are poured, in a single step, into the top of the tube of a measuring device with a height of 60 cm and a diameter of 4 cm ending in a closed cubic chamber with an edge height of 20 cm. The filtration device is placed on a side face of this chamber. The air containing the air-borne particles released during the fall of the granules is sucked off for 60 seconds and the particles are thus collected on the filter. The filter is recovered and weighed. The air-borne particles content of the granules analyzed, expressed in milligrams, is represented by the difference in filter weight before and after the analysis, with respect to the mass of granules analyzed (30 g) and expressed as a percentage.

Moreover, the method of measuring the degree of friability consists in agitating 50 g of granules in a 500 ml, glass, wide-necked bottle in the presence of a steel ball for 15 min. All the granules and fine particles formed are collected and dry sieved through a sieve with a mesh size equal to 0.15 mm. The degree of friability is the ratio, expressed as a percentage, of the weight of fine particles with a size less than 0.15 mm, formed during the agitation, to the weight of the granules analyzed (i.e. 50 g).

Moreover again, the following definitions are used hereinbelow for the expressions "wettability time", "degree of dispersibility" and "degree of suspensibility".

The wettability time is measured according to the MT 53.3.1 technique described in the CIPAC Handbook, Volume 1, pages 966–967, edited by G. R. Raw in 1970. It consists essentially of measuring the wetting time of 5 g of granules poured onto 100 ml of water.

The degree of dispersibility is measured according to the following technique. 10 g of granules are poured into a 250 ml measuring cylinder containing 250 ml of hard water defined in Method 18.1.4 described in the CIPAC Handbook, Volume 1, pages 875–878. The measuring cylinder and its contents are inverted 10 times, the contents are then poured onto a sieve with a mesh size of 160 μm, and the residue is dried and weighed; the degree of dispersibility is then expressed by the percentage of granule passing through the sieve.

The degree of suspensibility is measured according to the MT 15.1, note 4, technique described in the CIPAC Handbook, Volume 1, pages 861–865. It consists essentially in pouring 2.5 g of granule into a 250 ml measuring cylinder containing 250 ml of hard water, in inverting the measuring cylinder and its contents 30 times, in allowing to stand for 30 min and in measuring the mass of material contained in the lower 25 ml of the measuring cylinder (10% of the volume of the measuring cylinder); the degree of suspensibility is then expressed by the percentage of material remaining in suspension in the upper 90% of the measuring cylinder.

The compositions according to the invention are solid concentrated compositions comprising at least 2 agriculturally-active materials, characterized in that they are a mixture of concentrated compositions which are provided in the form of water-dilutable granules, in that their air-borne particles content is less than 0.1%, preferably less than 0.01%,) and in that each water-dilutable granule comprises at most one active material.

The concentrated compositions composing the compositions which are the subject of the invention will be denoted in the continuation of the disclosure under the term of "granule categories".

The term water-dilutable granules is understood to mean any granule species which can give rise, after dilution in water, to an aqueous solution or dispersion which can be conveniently sprayed by the farmer by means of a spraying device and give rise to a homogeneous distribution of the active materials on the surface to be treated. It can be a granule whose constituents are soluble at the use dose. It can also be a granule whose active material is, at the use dose, either insoluble or dissolved after a time greater than the usual time for the preparation of the slurry. Such a granule can be provided in the form of dispersible granules optionally comprising an effervescent agent and gives rise to a stable and homogeneous suspension. Water-dilutable granules thus constitute an array including dispersible granules and soluble granules.

According to an advantageous aspect of the invention, the solid concentrated compositions of the invention are characterized in that the median diameter of the granules is between 0.150 and 10 mm, preferably between 0.200 and 4 mm. The term median diameter is understood to mean the median of the particle size distribution of the granules which is measured by the following method. 50 g of granules to be analyzed are passed through a stack of successive sieves, with mesh sizes ranging from 5 mm to 0.074 mm. After sieving for 10 min, the residues retained on each sieve are individually weighed and expressed as a percentage relative to the mass of granules analyzed. The median diameter is calculated by a conventional statistical method, such as regression, by assuming that the data obtained are distributed according to a normal law.

According to another aspect of the invention, the solid concentrated compositions of the invention are characterized in that the minimum size of the water-dilutable granules is greater than 0.05 mm, preferably greater than 0.15 mm. The minimum size of the granules is measured by a dry sieving or wet sieving method or alternatively by an optical method, for example by diffraction of a laser beam.

According to another aspect of the invention, the solid concentrated compositions of the invention are characterized in that the degree of friability of the dilutable granules is between 0 and 8%, preferably between 0 and 5%. The degree of friability is measured according to the method defined above.

According to another aspect of the invention, the solid concentrated compositions of the invention are characterized in that the ratio of the median diameters of any 2 granule categories is less than or equal to 10, preferably less than or equal to 2. In this case, the solid concentrated composition is more stable, that is to say the homogeneous nature of the mixture is better maintained during storage and transportation.

According to another aspect of the invention, the solid concentrated compositions according to the invention are characterized in that the active material content of each of the granules containing an active material is between 5 and 100%, preferably between 50 and 90%. It is well understood that the agriculturally-active materials present in the solid concentrated compositions according to the invention are agrochemical products and can be either entirely herbicidal or entirely fungicidal or entirely insecticidal or, finally, a combination of fungicidal and insecticidal active materials.

According to another aspect of the invention, the solid concentrated composition, which is the subject of the invention, can combine active materials which are incompatible when they are mixed in the finely divided powder form (that is to say, an array of particles from 1 to 30 $\mu$m, preferably 2 to 20 $\mu$m). Thus is the case, on the one hand, when the milling of the said mixture is not possible due to the existence of a low melting-point eutectic between two or a number of these active materials, the temperature rise resulting from the milling then having the effect of causing melting and partial recrystallization of the treated mixture. Thus is also the case, on the other hand, when, due to chemical reactions, especially acid/base reactions, the amount of at least one active material present in the finely divided powder mixture decreases after storing under the usual conditions of use of agrochemical products, that is to say during a period of time ranging up to 2 years and at a temperature which can vary between −20 and +45° C. The invention thus makes it possible to combine, in the form of ready-to-use compositions, incompatible active materials which cannot be combined by means of known solid concentrated compositions which require mixing of these active materials in the form of finely divided particles, especially wettable powders and dispersible granules. This aspect of the invention is not, however, in any way limiting of the invention.

According to another aspect of the invention, at least one of the dilutable granule categories comprising an agriculturally-active material is a dispersible granule.

Preferably, the dilutable granules of the compositions according to the invention additionally comprise:

a wetting agent, that is to say a compound which makes it possible for the granule to rapidly enter into the water, a dispersing agent, that is to say a compound which provides that the particles are held in suspension in the slurry of use and which makes it possible for the granule to rapidly disintegrate in water, an effervescent agent, that is to say an agent or compound capable of releasing a gas such as $CO_2$ and, consequently, of making it easier for the granule to disintegrate in the water and for its constituent particles to be dispersed, a vehicle or filler which is soluble or insoluble in the water.

Mention may be made, as compounds which can be used as wetting agents, of, for example, salts of alkyl aryl sulphonate type, especially alkali metal alkyl naphthalenesulphonates, salts of polycarboxylic acids, polycondensates of ethylene oxide with fatty alcohols or with fatty acids or with fatty amines, substituted phenols (especially alkylphenols or arylphenols) or salts of esters of sulphosuccinic acids.

Mention may be made, as compounds which can be used as dispersing agents, of, for example, polymers of aryl sulphonate type, especially the alkali metal polynaphthalenesulphonates obtained by condensation of (alkyl) aryl sulphonates with formaldehyde, lignosulphonates, polyphenylsulphonates, salts of polyacrylic acids, salts of lignosulphonic acids, salts of phenolsulphonic or naphthalenesulphonic acids, taurine derivatives (especially alkyl taurates), phosphoric esters of polyoxyethylated phenols or alcohols, esters of fatty acids and of polyols, and the derivatives of the above compounds containing sulphate, sulphonate and phosphate functional groups.

The effervescent agent advantageously consists of a pair of products such as a carbonate (or hydrogencarbonate, preferably alkali metal) and an acid (preferably solid and weak). It is well understood that in the case where the base of the mixture comprises an active material having at least one acid functional group, the effervescent agent can consist solely of a, preferably alkali metal, carbonate or hydrogencarbonate. The ratio by mass of the acid, or the active material of the base of the mixture having at least one acid functional group, to the carbonate is generally between 0.3 and 2, preferably between 0.5 and 1.

The vehicle is a natural or synthetic, organic or inorganic solid material. This vehicle is generally inert and acceptable in agriculture, especially on the treated plant. It can be chosen, for example, from clay, diatomaceous earth, natural or synthetic silicates, silica, resins, waxes, solid fertilizers, soluble or insoluble inorganic salts, organic derivatives, and polysaccharide compounds such as starch, cellulose, sugars or lactose.

Preference is given, among usable vehicles, to hydrophilic vehicles which have a disintegrating action, that is to say which facilitate rupturing of the granule into its constituent particles in the presence of water. Mention may be made, as compounds of this type, of bentonites (natural or activated), starch and its derivatives (especially alkylstarches and carboxyalkylstarches), celluloses (especially microcrystalline cellulose) and cellulose derivatives (especially carboxyalkylcellulose), alginates, soluble inorganic salts or crosslinked polyvinylpyrrolidone.

When the water-dilutable granules of the compositions according to the invention are dispersible granules, they can contain, in addition to the constituents indicated above, other compounds, especially compounds more specifically having a binding action, that is to say a compound of polymer type which helps in the cohesion and in the implementation of the granules. These compounds which have a binding action can be either compounds distinct from those mentioned above or else they can be these same compounds insofar as they are capable of having a double action. It is preferable to use, as compounds or agents of this type, agents such as gums, especially gum arabic; adhesives, especially dextrin,; sugars, especially glucose and lactose; cellulose derivatives, especially alkylcellulose and carboxyalkylcellulose; starch; polymers, especially polyvinylpyrrolidone, poly(vinyl alcohol), polyethylene glycol, polyacrylate, poly(vinyl acetate); soluble waxes or alkali metal silicates.

The binding agent and the agent or vehicle which has disintegrating properties do not have conflicting effects insofar as the action of the binding agent is exerted in the solid state in order to bind together the various solid particles of the compositions according to the invention and that the action of the agent which has disintegrating properties is exerted in the liquid state when the compositions according to the invention are dispersed in the water.

Still in addition to the constituents described above, the water-dilutable granules of the compositions according to the invention can contain anti-foaming agents, sequestering agents, stabilizing agents, penetrating agents, preserving agents, adhesives, anticlumping agents, dyes and others.

Of course, the compositions according to the invention can additionally contain any solid or liquid additive corresponding to the usual techniques for agrochemical formulation.

The amounts of the constituents of the granules, which are distinct from an agriculturally-active material, are generally:

between 0.1 and 8% for the wetting agent, preferably between 0.5 and 5%;

between 0.3 and 25% for the dispersing agent, preferably between 2 and 20%;

between 0 and 80% for the effervescent agent, preferably between 0 and 50%;

between 0 and 50% for the vehicle, preferably between 0 and 30%.

It is preferable, among all the constituents of the granules according to the invention, to additionally choose those which, by their nature and their dose in the compositions according to the invention, provide granules having:

a wettability time less than 5 min, preferably less than 2 min, a degree of dispersibility greater than 85%, preferably greater than 92%, a degree of suspensibility greater than 50%, preferably greater than 70%.

The water-dilutable granules of the compositions according to the invention are prepared according to processes known per se.

Thus, when the dilutable granules are dispersible granules, their preparation is generally carried out from wettable powders having the same chemical composition as the granules, these wettable powders then being moistened, shaped and finally dried.

In order to obtain these wettable powders, the active material is intimately mixed in suitable mixers with the additional substances, optionally impregnated on the porous vehicle, and the mixture is milled with mills or other suitable grinders.

According to a first method of preparation of granules which can be used in the invention, the wettable powders are moistened by direct addition of liquid water (from 1 to 20% water, preferably 10 to 18% water) and then this moistened powder, which has the consistency of a paste, is extruded through a grid or perforated plate so as to obtain an extrudate in the form of a multiplicity of elongated cylinders, which are sometimes called sausages or even spaghetti, which are then broken lengthwise so as to produce a multitude of small short cylinders which constitute the granules according to the invention. As the latter are moist, it is then sufficient to dry them (for example at more than 50° C., preferably at 80° C., in a ventilated atmosphere) in order to obtain the true granules according to the invention which can be marketed.

According to a second method for the preparation of granules which can be used in the invention, the wettable powders are moistened by spraying with water (from 5 to 35% water, preferably 20 to 30% water) in a fluidized bed formed with the wettable powder. This operation leads directly to the formation of moist granules, which it is then sufficient to dry in order to obtain the true granules according to the invention which can be marketed.

According to a third method for the preparation of granules which can be used in the invention, the wettable powders are moistened by direct spraying with liquid water (from 1 to 20% water, preferably 10 to 18% water) on the wettable powder situated on a sloping and rotating plate. The fact that this plate rotates makes it indeed possible for the grains of the powder to remain dissociated from each other. Spraying water onto these moving grains also leads to the formation of moist granules, which it is then sufficient to dry (for example at more than 80° C., preferably at 100° C., in a ventilated atmosphere), in order to obtain the true granules according to the invention which can be marketed.

According to a fourth method for the preparation of granules which can be used in the invention (known as atomization), a concentrated suspension is prepared from wettable powder by direct addition of liquid water (from 20 to 70% water, preferably 30 to 50% water); this suspension is then sprayed into a hot air drier (atomizer) which makes it possible to obtain fine and dry granules by rapid evaporation of the water contained in the suspension droplets; the temperature of the drying air is generally between 120 and 300° C., preferably between 150 and 250° C.

When the water-dilutable granules are effervescent granules, their preparation is carried out by dry agglomeration of the constituents of the wettable powder, additionally comprising an effervescent agent, by a compacting technique, preferably at ambient temperature or at least below 50° C. The apparatus used for this technique is preferably composed of two rotating cylinders, with parallel axes, applied very tightly against each other and each driven by a rotary movement in opposite directions.

It is well understood that the methods for the preparation of the granule categories of a composition according to the invention, which have just been described, are not necessarily identical for all the granule categories of the same composition according to the invention.

However, in the case where the median diameter ratio of the granules of any 2 granule categories of a composition according to the invention is less than or equal to 10, recourse to the same method of preparation is preferred. Moreover, in this case, the homogeneity in shape of the granules improves the stability of the solid concentrated composition according to the invention, that is to say its ability to better retain a homogeneous nature after storing and transportation.

A description is now given of an embodiment of the solid concentrated compositions according to the invention, starting from granules whose method of preparation has been described above.

Figure 1:
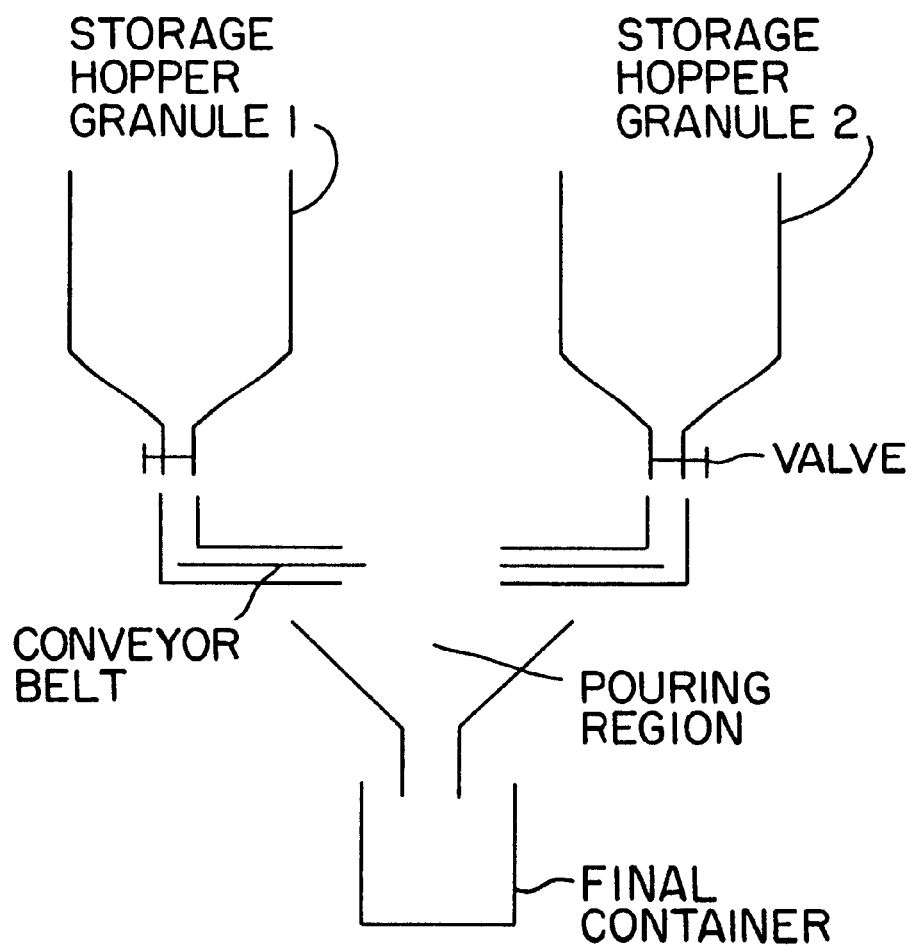
FIG. 1 provides a schematic diagram which illustrates one embodiment of the present invention.

The solid concentrated compositions according to the invention are obtained from the water-dilutable granules defined above by any process which makes possible intimate mixing of the granules in the desired proportions.

Such a mixing process is represented in FIG. 1, in which a solid concentrated composition comprising 2 agriculturally-active materials is prepared from 2 granule categories, each comprising one active material. Each granule category is stored in a hopper. An adjustable valve makes it possible to run a set flow rate of granules, which are conveyed, for the 2 granule categories, by 2 conveyor belts which move in opposite directions and which end in a common pouring area where the granules are mixed and accumulate in the storage container. The flow rates are adjusted so that their ratio is equal to the desired ratio for the 2 active materials. Such a process is particularly advantageous in that it makes it possible to respect the characteristics defined for the compositions according to the invention.

The solid concentrated compositions according to the invention are used in practice by putting them in tanks containing water; these tanks can optionally be stirred. The mixture thus obtained, known as spray slurry, can be used as is in order to be applied to the cultivated or non-cultivated surfaces to be treated.

Another subject of the present invention is a containerization system comprising:

a) a solid concentrated agrochemical composition according to the present invention, b) a bag, the wall of which is a film consisting of a water-soluble or water-dispersible film-forming material, the said bag being closed and containing the said composition.

The term water-dispersible material must be understood as meaning a material which, under the effect of normal stirring (such as commonly carried out by farmers in spray tanks), leads to a dispersion of fine particles with a size less than 40 $\mu$m, preferably 15 $\mu$m.

According to an advantageous aspect of the invention, the amount of composition according to the invention present in a containerization system as defined above is an effective amount for treating a given area of cultivated or non-cultivated ground.

With a view to improving the contact between the water of the spray tank and the containerization system according to the invention and/or the composition according to the invention, it is preferable to use containerization systems which are free of gas pockets. These containerization systems are generally such that, the bag being sealed, it is not possible to see the least space between the solid concentrated compositions according to the invention and the wall of the bag and/or that it is not possible, manually, to pull the wall of the bag away from the dilutable granules. This therefore corresponds to an absence of air pockets or, in other words, to a maximum degree of filling for the form of the bag under consideration. In practice, it is advantageous to fill the bags of the invention at an absolute pressure less than 200 millibar, preferably less than 150 millibar, so as to provide for adherence of the film to the solid concentrated composition at the time of bagging and before final sealing of the bag, and even up to final use of the containerization systems according to the invention, even after storing.

According to another aspect of the invention, the amount of solid concentrated composition according to the invention contained in the bag is between 1 g and 3 kg, preferably between 5 g and 1 kg, still more preferentially between 100 g and 1 kg.

According to another aspect of the invention, the water-soluble or water-dispersible film-forming material constituting the wall of the bag can be of very varied type. It is preferably water-soluble. It generally concerns polymeric material such as polyethylene oxide, polyethylene glycol, starch or modified starch; alkyl- or hydroxyalkylcellulose, such as hydroxymethylcellulose, hydroxyethylcellulose or hydroxypropylcellulose; carboxymethylcellulose; poly (vinyl ether)s such as poly(methyl vinyl ether) or poly(2-methoxyethoxyethylene); poly(2,4-dimethyl-6-triazinylethylene); poly(3-morpholinylethylene); poly(N-1, 2,4-triazolylethylene); poly(vinylsulphonic) acid; polyanhydrides; low molecular weight urea-formaldehyde or melamine-formaldehyde resins; poly(2-hydroxyethyl methacrylate); polyacrylic acid and its homologues.

The preferred materials for constituting the bags are polyethylene oxide, methylcellulose and poly(vinyl alcohol) (PVA). A preferred material for constituting the walls of the bag is poly(vinyl alcohol). When PVA is used, it is preferable to use a poly(vinyl acetate) (or another vinyl ester) which is partially or entirely hydrolyzed or alcoholyzed, that is to say hydrolyzed or alcoholyzed to 40–100%, preferably 80–99%. Copolymers or other derivatives of these polymers can also be used.

According to another aspect of the invention, the bag containing the solid concentrated composition according to the invention comprises a first non-planar film made of water-soluble or water-dispersible material, this first film being adjacent to a second film, itself made of water-soluble or water-dispersible material, along a continuous sealing line bonding these two films, the said line constituting a closed line which is not intersected and which delimits an essentially planar area.

According to another aspect of the invention, the bag containing the solid concentrated composition according to the invention consists of a single film and preferably comprises at least three sealing areas, two of which are substantially rectilinear and coplanar and cut by the third into two substantially limited areas.

According to a variant of the invention, the containerization systems described above can additionally comprise an outer container. This outer container has walls consisting of a system containing at least two layers bonded to each other, one made of flexible cardboard, known as kraft liner, and the other made of polyethylene. This two-layer system can additionally comprise a third layer bonded to the polyethylene and consisting of aluminium.

The containerization systems according to the invention are prepared according to packaging techniques known per se. They are used in practice by putting them into tanks containing water; these tanks can optionally be stirred and can, in certain cases, be carried on the backs of the users. The mixture thus obtained, known as spray slurry, can be used as is in order to be applied on the cultivated or non-cultivated surfaces to be treated.

The examples below are given by way of illustration of the compositions and containerization systems according to the invention. The mixing process used in these examples is that described above.

EXAMPLE 1

Solid Concentrated Compositions Based on Diflufenican and Isoproturon

Iosproturon and diflufenican are 2 active materials used in killing weeds in cereals which are described in the Pesticide Manual, 9th Edition, published by the British Crop Protection Council.

Many concentrated compositions comprising these 2 active materials in different ratios are marketed in order to satisfy the various requirements of farmers according to the specific populations of adventitious species which they have to control. The different ratios (isoproturon/diflufenican) desired are: 5, 8, 10, 10.7, 12, 25.

A dispersible granule containing 75% diflufenican is prepared in the following way.

The following ingredients are dry mixed in the form of pulverulent solids:

| | |
|---|---|
| Diflufenican | 750 g |
| Sodium alkyl naphthalenesulphonate | 20 g |
| Sodium polyphenylsulphonate | 100 g |
| Sodium lignosulphonate | 130 g |

This mixture is granulated by atomization.

A dispersible granule containing 80% isoproturon is prepared. The following ingredients are dry mixed in the form of pulverulent solids:

| | |
|---|---|
| Isoproturon | 800 g |
| Sodium polycarboxylate | 80 g |
| Sodium dodecyl benzenesulphonate | 20 g |
| Sodium lignosulphonate | 100 g |

This mixture is, like the above, granulated by atomization.

Finally, an inert granule (without active material) is prepared by mixing the following ingredients in the form of pulverulent solids:

| | |
|---|---|
| Silicoaluminate | 800 g |
| Sodium polycarboxylate | 80 g |
| Sodium dodecyl benzenesulphonate | 20 g |
| Sodium lignosulphonate | 100 g |

Solid concentrated compositions according to the invention are obtained by mixing predetermined amounts of the granules prepared above by a device analogous to that described in FIG. 1. The isoproturon/diflufenican ratios of the concentrated compositions, and the amounts of granules used, are combined in the table below.

| Weight of dispersible diflufenican granules (in g) | Weight of dispersible isoproturon granules (in g) | Weight of inert granules (in g) | Isoproturon/diflufenican ratio |
|---|---|---|---|
| 166.7 | 781.2 | 52.1 | 5 |
| 111.1 | 833.3 | 55.6 | 8 |
| 88.9 | 833.3 | 77.8 | 10 |
| 81 | 843.7 | 72.3 | 10.7 |
| 74.1 | 833.3 | 92.6 | 12 |
| 40 | 937.5 | 22.5 | 25 |

The granules of the solid concentrated compositions thus prepared have a median diameter of 250 µm. Their air-borne particles content is 0.01% and their degree of friability is 1%. After mixing with water, these granules disperse very rapidly and give rise to a homogeneous and stable suspension.

EXAMPLE 2

Solid Concentrated Compositions Based on Carbetamide and Dimefuron

Carbetamide and dimefuron are 2 herbicidal active materials which are described in the Pesticide Manual, 9th Edition, published by the British Crop Protection Council.

Two concentrated compositions comprising these 2 active materials at 2 different ratios are marketed. These ratios (carbetamide/dimefuron) are: 3 and 2.

A dispersible granule containing 60% carbetamide is prepared in the following way.

The following ingredients are dry mixed in the form of pulverulent solids;

| | |
|---|---|
| Carbetamide | 600 g |
| Precipitated silica | 117 g |
| Sodium alkyl taurate | 15 g |
| Sodium polynaphthalenesulphonate | 80 g |
| Sodium alkyl naphthalenesulphonate | 20 g |
| Silicoaluminate | 153 g |
| $C_{13}$ Fatty alcohol | 5 g |
| Sodium alkyl sulphosuccinate | 10 g |

This mixture is granulated using a fluidized bed granulator.

A dispersible granule containing 60% dimefuron is prepared. The following ingredients are dry mixed in the form of pulverulent solids:

| | |
|---|---|
| Dimefuron | 600 g |
| Silicoaluminate | 80 g |
| Sodium polynaphthalenesulphonate | 80 g |
| Sodium alkyl naphthalenesulphonate | 20 g |
| Maize starch | 40 g |
| $C_{13}$ Fatty alcohol | 5 g |
| Precipitated silica | 5 g |
| Silicoaluminate | 170 g |

This mixture is, like the above, granulated using a fluidized bed granulator. By mixing, as in Example 1, the granules thus prepared, solid concentrated compositions are obtained whose carbetamide/dimefuron ratio is shown, with the amounts of granules used, in the table below.

| Weight of dispersible carbetamide granules (in g) | Weight of dispersible dimefuron granules (in g) | Carbetamide/ dimefuron ratio |
| --- | --- | --- |
| 750 | 250 | 3 |
| 667 | 333 | 2 |

The granules of the solid concentrated compositions thus prepared have a median diameter of 1 mm. Their air-borne particles content is 0.08% and their degree of friability is 7%. After mixing with water, these granules disperse very rapidly and give rise to a homogeneous and stable suspension.

EXAMPLE 3

Solid Concentrated Compositions Based on Fosetyl-Al and Mancozeb

Fosetyl-Al and mancozeb are 2 fungicidal active materials which are useful for vines described in the Pesticide Manual, 9th Edition, published by the British Crop Protection Council.

It is desirable to have available 2 concentrated compositions comprising these 2 active materials in a fosetyl-Al/mancozeb ratio equal to 1 and 1.7.

A dispersible granule containing 80% fosetyl-Al is prepared in the following way.

The following ingredients are dry mixed in the form of pulverulent solids:

| | |
| --- | --- |
| Fosetyl-Al | 800 g |
| Ethoxylated alkylphenol | 52 g |
| Ethoxylated alkylphenol | 10 g |
| Sodium acetate | 20 g |
| Sodium lignosulphonate | 44 g |
| Silicone oil | 5 g |
| Silicoaluminate | 38 g |
| Precipitated silica | 17 g |

This mixture is granulated by atomization.

A dispersible granule containing 75% mancozeb is also prepared by first of all dry mixing the following ingredients, milled to the form of pulverulents solids:

| | |
| --- | --- |
| Mancozeb | 750 g |
| Sodium dioctyl sulphosuccinate | 20 g |
| Sodium polynaphthalenesulphonate | 230 g |

This mixture is also granulated by atomization.

Solid concentrated compositions according to the invention are obtained by mixing, as in the above examples, the 2 granules thus prepared. The fosetyl-Al/mancozeb ratios of the concentrated compositions, and the amounts of granules used, are combined in the table below:

| Weight of dispersible fosetyl-Al granules (in g) | Weight of dispersible mancozeb granules (in g) | Fosetyl-Al/ mancozeb ratio |
| --- | --- | --- |
| 500 | 500 | 1 |
| 626 | 374 | 1.67 |

The granules of the solid concentrated compositions thus prepared have a median diameter of 300 μm. Their air-borne particles content is 0.01% and their friability is 1.7%. After mixing with water, these granules disperse very rapidly and give rise to a homogeneous and stable suspension.

EXAMPLE 4

Containerization Systems Comprising Solid Concentrated Compositions Based on Diflufenican and Isoproturon 40 g of each of the mixtures based on diflufenican and on isoproturon of Example 1 are each introduced into a pocket consisting of a poly(vinyl alcohol) [poly(vinyl acetate) hydrolyzed to 88%] film which is soluble in cold water. This film was thermoformed, that is to say that it was deformed by heat and that it was made to take up, by suction, the form of a pocket given by a matrix. A second film is placed on the said pocket and is fixed to the latter by heat welding, simultaneously with the creation of vacuum by means of a pump giving rise to an absolute pressure of 100 millibar. No free space is observed between the dilutable granules and the wall of the bags obtained.

Each of these bags is thrown into a tank containing 100 liters of stirred water. The PVA film of each of the bags fragments and releases the granules which disperse homogeneously throughout the tank. The PVA film dissolves after 5 minutes.

EXAMPLE 5

Containerization Systems Comprising Solid Concentrated Compositions Based on Carbetamide and on Dimefuron 100 g of each of the mixtures of Example 2 are each introduced into a poly(vinyl alcohol) [poly(vinyl acetate) hydrolyzed to 88%] sachet which is soluble in cold water according to a procedure identical to that of Example 4. All surface element of the sachet is in contact with the granules of the solid compositions, so that no air pocket is observed to be present.

Each of the bags obtained is thrown into a tank containing 100 liters of stirred water. The bag fragments and releases the granules which disperse homogeneously. The PVA film dissolves after 5 minutes.

EXAMPLE 6

Containerization Systems Comprising Solid Concentrated Compositions Based on Fosetyl-Al and on Mancozeb 500 g of each of the mixtures of Example 3 are each introduced into a poly(vinyl alcohol) [poly(vinyl vinylacetate) hydrolyzed to 88%] sachet which is soluble in cold water. This sachet was obtained from a single rectangular film which received two perpendicular welding lines. After introduction of the granules, the bag receives a third welding line by heat sealing.

Each of the bags obtained is treated as in Example 5. The same result is obtained.

What is claimed is:

1. Solid concentrated compositions comprising a mixture of at least two agriculturally-active categories of material in concentrated form of water-dilutable granules, wherein said granules have an air-borne particle content of less than 0.1%, and, each water-dilutable granule comprises at most one active material.

2. The compositions according to claim 1, characterized in that the granules have a median diameter of between 0.150 and 10 mm.

3. The compositions according to claim 1, characterized in that the water-dilutable granules have a minimum size that is greater than 0.05 mm.

4. The compositions according to claim 1, characterized in that the dilutable granules have a degree of friability that is between 0 and 8%.

5. The compositions according to claim 1, characterized in that the ratio of the median diameters of any 2 granule categories is less than or equal to 10.

6. The compositions according to claim 1, characterized in that the active material content of each of the granules containing an active material is between 5 and 100%.

7. The compositions according to claim 1, characterized in that the combination of active materials are incompatible with one another when the individual component is mixed in a finely divided powder form.

8. The compositions according to claim 1, characterized in that the water-dilutable granules include dispersible granules and soluble granules.

9. The compositions according to claim 1, characterized in that at least one of the dilutable granule categories comprising an agriculturally-active material is a dispersible granule.

10. The compositions according to claim 1, characterized in that the dilutable granules additionally comprise at least one additional component selected from a wetting agent, a dispersing agent, an effervescent agent and a vehicle.

11. The compositions according to claim 1, characterized in that the amounts of the additional components, which are distinct from the agriculturally-active materials, are:
   between 0.1 and 8% for the wetting agent;
   between 0.3 and 25% for the dispersing agent;
   between 0 and 80% for the effervescent agent; and
   between 0 and 50% for the vehicle.

12. The compositions according to claim 1, characterized in that the granules have a wettability time less than 5 min, a degree of dispersibility greater than 85%, and a degree of suspensibility greater than 50%.

13. A containerization system comprising:
   a) a solid concentrated agrochemical composition according to claim 1,
   b) a bag, the wall of which is a film formed from a water-soluble or water-dispersible film-forming material that is
   closed and contains said composition.

14. The containerization system according to claim 13, characterized in that said closed bag is free of gas pockets.

15. The containerization system according to claim 13, characterized in that the bag is sealed so that it is not possible to see the least space between the solid concentrated compositions and the wall of the bag and/or that it is not possible, manually, to pull the wall of the bag away from the dilutable granules.

16. The containerization system according to claim 13, characterized in that the amount of solid concentrated composition contained in the bag is between about 1 g and about 3 kg.

17. The containerization system according to claim 13, characterized in that the bag is formed from a material chosen from polyethylene oxide methylcellulose or poly (vinyl alcohol).

18. The containerization system according to claim 13, characterized in that the bag containing the solid concentrated composition comprises, a first non-planar film made of water-soluble or water-dispersible material, this first film being adjacent to a second film, itself made of water-soluble or water-dispersible material, along a continuous sealing line bonding these two films, said sealing line constituting a closed line which is not intersected and which delimits an essentially planar area.

19. The containerization system according to one of claim 13, characterized in that the bag containing the solid concentrated composition is formed from a single film with at least three sealing areas, two of which are substantially rectilinear and coplanar and cut by the third into two substantially limited areas.

20. The containerization system according to claim 13, further including an outer container.

21. A process for the preparation of a fluid mixture to be applied to cultivated or non-cultivated surfaces to be treated, characterized in adding to water in a spray tank a solid concentrated composition according to claim 1.

22. The compositions according to claim 2, wherein the median diameter of the granules is between 0.200 and 4 mm.

23. The compositions according to claim 3, wherein the water-dilutable granules have a size that is greater than 0.15 mm.

24. The compositions according to claim 4, characterized in that the degree of friability of the dilutable granules is between 0 and 5%.

25. The compositions according to claim 5, characterized in that the ratio of the median diameters of any 2 granule categories is less than or equal to 2.

26. The compositions according to claim 6, characterized in that the content of the active material is between 50 and 90%.

27. The compositions according to claim 10, where the additional component quantities are:
   for the wetting agent, between 0.5 and 5%;
   for the dispersing agent, between 2 and 20%;
   for the effervescent agent, between 0 and 50%; and
   between 0 and 50% for the vehicle.

28. The compositions according to claim 12, characterized in that the granules have a wettability time less than 2 min, a degree of dispersibility greater than 92%, and a degree of suspensibility greater than 70%.

29. The containerization system according to claim 16, characterized in that the amount of solid concentrated composition is between 5 g and 1 kg.

30. The containerization system according to claim 29, characterized in that the amount of solid concentrated composition in the bag is between 100 g and 1 kg.

31. A process for the preparation of a fluid mixture intended to be applied to cultivated or non-cultivated surfaces to be treated, characterized in adding a spray tank a containerization system according to claim 13.

32. An agrochemical composition comprising:
   a first water-dilutable granule comprising, at most, one first agriculturally active material in concentrated form,
   a second water-dilutable granule comprising, at most, one second agriculturally active material in concentrated form,
   wherein the composition has an air-borne particle content of less than 0.1%.

* * * * *